US011013777B2

(12) United States Patent
Van der Saag et al.

(10) Patent No.: US 11,013,777 B2
(45) Date of Patent: May 25, 2021

(54) ARONIA EXTRACT FOR ENHANCING REACTION TIME AND ATTENTION

(71) Applicant: BioActor BV, Maastricht (NL)

(72) Inventors: Antonie Johannes Van der Saag, Maastricht (NL); Mandy Lambrix, Maastricht (NL); Yala Stevens, Maastricht (NL)

(73) Assignee: BioActor BV, Maastricht (NL)

(*) Notice: Subject to any disclaimer, the term of this patent is extended or adjusted under 35 U.S.C. 154(b) by 0 days.

(21) Appl. No.: 16/484,611

(22) PCT Filed: Feb. 9, 2018

(86) PCT No.: PCT/EP2018/053286
§ 371 (c)(1),
(2) Date: Aug. 8, 2019

(87) PCT Pub. No.: WO2018/146255
PCT Pub. Date: Aug. 16, 2018

(65) Prior Publication Data
US 2020/0030400 A1    Jan. 30, 2020

(30) Foreign Application Priority Data

Feb. 10, 2017  (EP) .................................... 17155575
May 3, 2017    (EP) .................................... 17169176

(51) Int. Cl.
*A61K 36/73*     (2006.01)
*A61P 25/26*     (2006.01)
*A61K 31/7028*   (2006.01)
*A61K 9/00*      (2006.01)

(52) U.S. Cl.
CPC .......... *A61K 36/73* (2013.01); *A61K 31/7028* (2013.01); *A61P 25/26* (2018.01); *A61K 9/0053* (2013.01)

(58) Field of Classification Search
None
See application file for complete search history.

(56) References Cited

U.S. PATENT DOCUMENTS

2009/0176718 A1* 7/2009 Ribnicky ............... A61K 36/45
                                                     514/27
2013/0034530 A1* 2/2013 Fantz ..................... A23L 33/15
                                                     424/94.2

FOREIGN PATENT DOCUMENTS

KR    20160074249 A    6/2016
KR    20160088622 A    7/2016
KR    20160088623 A    7/2016

OTHER PUBLICATIONS

Stefka V. et al. Memory Effects of Aronia melanocarpa Fruit Juice in a Passive Avoidance Test in Rats. Folia Medica 56(3)199-203, Jul. 2014. (Year: 2014).*
Lee H. et al. Cognitive Enhancing Effect of Aronia melanocarpa Extract Against Memory Impairment Induced by Scopolamine in Mice. Evidence Based Complementary and Alternative Medicine 2016:Apr. 1-7, 2016. (Year: 2016).*
Wei, J. et al. Anthocyanidins from Black Chokeberry (*Aronia melanocarpa*) Delayed Aging Related Degenerative Changes of Brain. J of Agricultural and Food Chemistry 65(29)5973-5984, Jul. 26, 2017. (Year: 2017).*
Garcia-Flores, L. et al. DNA Catabolites in Triathelites: Effects of Supplementation with an Arnonia Citrus Juice. Food and Function 7(4)2084-2093, 2016. (Year: 2016).*
Anna Skarpanska-Stejnborn et al, "Effect of Supplementation With Chokeberry Juice on the Inflammatory Status and Markers of Iron Metabolism in Rowers",Journal of the International Society of Sports Nutrition, Biomed Central Ltd, vol. 11, No. 1, Oct. 1, 2014, p. 48.
M. Eftimov et al, "Effect of Aronia Melanocarpa Fruit Juice on Behavior of Rats Exposed to Social Isolation", Trakia Journal of Sciences, vol. 12, No. 12, Jan. 1, 2014, p. 123-126.
Stefka V. Valcheva-Kuzmanova et al., "Memory Effects of Aronia Melanocarpa Fruit Juice in a Passive Avoidance Test in Rats," Folia Medica, Vo. 56, No. 3, Jul. 1, 2014, pp. 199-203.
Hyeon Yong Lee et al, "Cognitive-Enhancing Effect of Aronia melanocarpa Extract Against Memory Impairment Induced by Scopolamine in Mice",Evidence-Based Complementary and Alternative Medicine, vol. 2016, Apr. 30, 2016, pp. 1-7.
Mirko Tomic et al, "Reduction of Anxiety-Like and Depression-Like Behaviors in Rats After One Month of Drinking Aronia Melanocarpa Berry Juice" ,Food & Function, vol. 7, No. 7, Jan. 1, 2016, pp. 3111-3120.
Nam Young Kim et al, "Enhancement of Cognitive Functions by Aronia melanocarpa Elliot Through an Intermittent Ultrasonication Extraction Process," Journal of Medicinal Food, vol. 19, No. 3, Mar. 1, 2016.
Extended European Search Report dated Aug. 1, 2017 in related International Application No. EP 17155575.8.
International Search Report and Written Opinion dated May 8, 2018 in related International Application No. PCT/EP2018/053286.

* cited by examiner

*Primary Examiner* — Ralph J Gitomer
(74) *Attorney, Agent, or Firm* — Dinsmore & Shohl LLP

(57) ABSTRACT

This invention relates to the use of an *Aronia* berry extract or a composition comprising said extract for enhancing the reaction time, attention, concentration and psychomotor control of a mammal, more in particular a human. The composition comprising the *Aronia* extract is formulated for oral ingestion.

16 Claims, 2 Drawing Sheets

A

B

C

D

A

B

C

A

B

ARONIA EXTRACT FOR ENHANCING REACTION TIME AND ATTENTION

FIELD OF THE INVENTION

This invention relates to an *Aronia* berry extract and its use in enhancing the reaction time, the psychomotor function and/or the attention of a mammal, more in particular a human.

BACKGROUND TO THE INVENTION

There is a great interest in improving attention/concentration, reaction time, psychomotor function and visual-motor coordination. The best-known and most widely consumed stimulant to increase attention and reaction time is caffeine. It is estimated that about 90% of the adults in North America daily consume caffeine. About 9 million tons of coffee were consumed in 2015. In addition to caffeine, several synthetically created drugs have been developed to increase attention and reaction time. They are beneficial to treat specific diseases, such as attention-deficit hyperactivity disorder, as well as to provide a mental boost for healthy humans, such as for performing high-intensity tasks, working late-night shifts, etcetera.

However, even as these synthetically created stimulants might be safe to be taken by healthy persons, people tend to see these supplements as medical drugs and are hesitant to consume them. In general, people are much more likely to take stimulants derived from natural sources. Therefore, there is a continuing need for naturally-derived products to improve attention and reaction time.

SUMMARY OF THE INVENTION

The inventors have surprisingly identified that an extract of *Aronia* berries provides for this effect and increases attention/concentration, reaction time, and psychomotor function and visual-motor coordination. More specifically, in one embodiment, the present invention provides the use of an *Aronia* berry extract in enhancing the reaction time of a mammal, preferably of a human. In another embodiment, the use of an *Aronia* berry extract is provided in enhancing the alertness of a mammal, preferably of a human. In still another embodiment, the use of an *Aronia* berry extract is provided in enhancing the psychomotor function of a mammal, preferably of a human.

*Aronia* is a genus within the Rosaceae family and originates from North America. The berries of these plants are often called chokeberries. Nowadays *Aronia* berries are widely distributed and in some countries cultivated as an industrial crop. *Aronia* berries are distinctive with a high content of polyphenols and possess one of the highest antioxidant activities among plant species measured with oxygen radical absorbance capacity which is mainly attributable to the anthocyanins. *Aronia melanocarpa* (black chokeberry) has a simple anthocyanin profile and has extensively been investigated. It has been confirmed that the berry polyphenols are bioavailable in humans. Thirty minutes post-ingestion, anthocyanins can be measured in plasma. Due to this relatively short time period, it is suggested that absorption of anthocyanins takes (partly) place in the stomach. There is poor absorption in the small intestine, so anthocyanin 'left overs' will pass into the large intestine. Anthocyanins are mostly glucuronidated (addition of glucuronic acid) representing approximately 55% of the total anthocyanins in plasma and urine. One of the main metabolites found in plasma is cyanidin-3-galactoside which represents around 65% of the total metabolites. These transformations can affect the biological activity of anthocyanins and lead to the reported health benefits associated with anthocyanins. It is already known that *Aronia* berries have antidiabetic, cardioprotective, hepatoprotective, antimutagenic and anticarcinogenic effects and serve as a powerful antioxidant.

Animal studies have also demonstrated that berry polyphenols and flavonoids may cross the blood-brain-barrier and accumulate in the brain. For instance, studies supplementing rats with *Aronia melanocarpa* juice indicated that the juice may have antidepressive and anxyolitic properties. There are multiple studies that suggest these antidepressive mood effects. These study results seem to suggest that *Aronia* has a sedative effect, rather than a stimulating effect. This assumption is further supported by a rat study that observed a reduction in horizontal and vertical movements after three weeks of daily supplementation with *Aronia melanocarpa* juice which indicates an anxiolytic effect. When an underlying disease was the cause of a decreased movement (hypokinesia), *Aronia melanocarpa* juice was able to partly antagonize the effects on locomotor activity.

Furthermore, it has been suggested that compositions comprising several ingredients, including *Aronia*, may improve the memory as indicated in RU93016375, describing a concentrate for soft drink containing grape juice, apple juice and a mixture of chokeberry, rosehip, hawthorn, pine and pear extract. Furthermore, KR20160074249 discloses an extract for immunological reinforcement, whereas KR20160088622 and KR20160088623 describe an extract for preventing and treating age-related diseases, more specifically dementia.

However, it should be underscored that there is a stark difference between (working) memory or cognition on the one hand and attention, reaction time, alertness and psychomotor control on the other hand. While all are (partially) cognitive features, there are important differences in between them. Attention or alertness is the ability to selectively process information, and it is assumed that it has a limited role in the retention of information. More specifically, alertness is a state of active attention by high sensory awareness such as being watchful and prompt to meet danger or emergency, being quick to perceive and act. On the other hand, memory is the ability to retain information in an accessible state. Working memory is often defined as the mental workspace where important information is kept in a highly active state, available for a variety of other cognitive processes. A consequence of these differences is that memory stimulants do not automatically imply an effect on attention, reaction time, concentration, alertness and psychomotor control and vice versa. For example, while caffeine and other stimulants are known to increase attention and reaction time, they do not influence/improve memory. In fact many previous studies have found that an increase in phasic or tonic alertness impairs cognitive control, even though overall response times are decreased. This counter-intuitive pattern of behavior is still poorly understood but could be explained in that cognitive control takes time to develop and that this is counteracted by an increased alertness as it reduces the time needed for stimulus encoding. No effect of *Aronia* on reaction time, attention, concentration, alertness or psychomotor control has been suggested or shown in the prior art. Therefore, the present invention provides the use of an *Aronia* berry extract exerting effects allowing improvement in reaction time alertness and attention, and in enhancing psychomotor function, in particular in mammals, preferably in humans. In addition thereto, the present invention provides the use of compositions comprising such an extract, wherein the extract is preferably in the form of a pill, powder, capsule, tablet, gel, beverage, chewing gum, chewable tablet, lozenge or troche.

In a preferred embodiment, the use of an *Aronia* berry extract as outlined herein above is characterized in that the *Aronia* berry extract comprises more than 10% anthocyanins, more preferably more than 13%, even more preferably at least 15% anthocyanins.

In another particular embodiment, the use of an *Aronia* berry extract according to the present invention is further characterized in that said *Aronia* berry extract comprises more than 25% total polyphenols, in particular at least 30%, more in particular at least 35% total polyphenols.

In yet another particular embodiment, the use is characterized in that the *Aronia* berry extract comprises at least 3, in particular at least 5%, more in particular at least 7% of cyanidin-3-glucoside.

In another embodiment, the present invention provides the use of a composition comprising between 50-1200 mg *Aronia* berry extract. This composition is preferably formulated in a daily dosage form comprising 1 to 90 mg of anthocyanins extracted from *Aronia* berries.

In a certain embodiment, the composition comprising *Aronia* berry extract is supplied in combination with one or more additional ingredients selected from a group consisting of: caffeine, taurine, theanine, inositol, guarana, magnesium, melatonin, ribose, carnitine, co-enzym Q10, alpha-glycerophosphocholine, alpha-lipoic acid and xylose.

In a specific embodiment, the composition is an oral composition and is in the form of a pill, powder, capsule, tablet, gel, beverage, chewing gum, chewable tablet, lozenge or troche.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
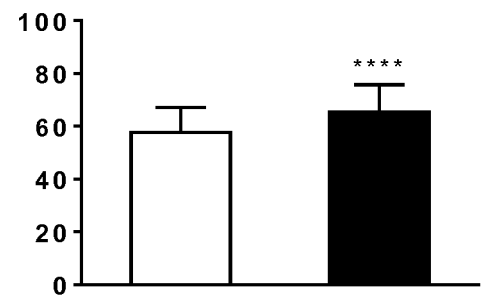
FIG. 1: Short-term effect of oral *Aronia* administration on attention/concentration based on Score Out test with (A) Total amount correct answers (Tg), (B) Total amount answers correct minus total mistakes (Tg-Tf), (C) Total amount finished (Tb), (D) Total amount finished, minus total mistakes, minus total missed numbers (Tb-FoMi). The raw-scores from the Score Out test have been transformed into norm-scores. Data are expressed as mean±SD (n=20), **** $P<0.0001$. Empty bars: baseline, black bars: treatment.
Figure 1:
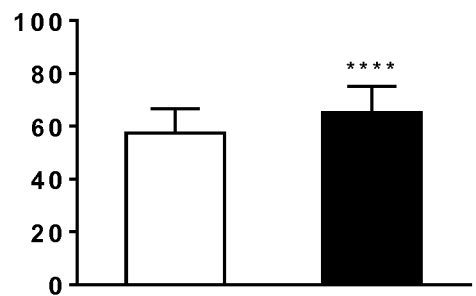
Figure 1:
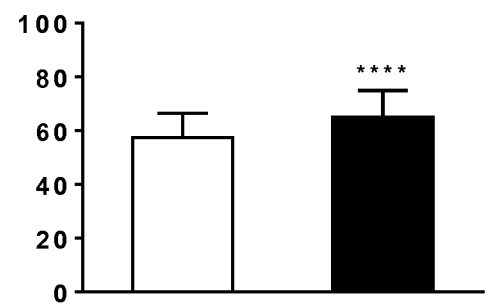
Figure 1:
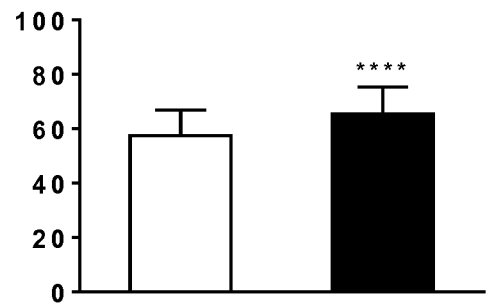

The present invention discloses the use of an *Aronia* berry extract, preferably an *Aronia melanocarpa* berry extract, in enhancing the reaction time, concentration, attention and/or psychomotor function of a mammal, in a preferred embodiment humans, in particular healthy humans. The extract is a powder that can be derived from fresh chokeberries or chokeberry juice. To obtain 1 kg of extract, approximately 90 kg of fresh berries are needed. Ethanol can be used as a solvent in the production process. The subject may be a healthy subject, e.g., a subject who desires increasing its attention, reaction time and mental energy. For example, the subject may be preparing for an intellectual or sportive challenge. A subject may also be a subject that is or will be sleep deprived, fatigued, drowsy or sleepy. A subject may be a subject who has or will have a substance-induced decline in concentration, attention and reaction time. A substance-induced decline may e.g. be an alcohol- or drug abuse-induced decline or a medicament-induced decline. A subject may be a subject having an injury-related decline in attention and reaction time. A subject may also be a healthy subject that wants to have more mental energy to gain the feeling that they can achieve more.

As used herein, the term "attention" refers to the ability to direct and focus cognitive activity on specific stimuli. It is the ability or power to concentrate mentally. Attention and concentration are used interchangeably herein.

As used herein, the term "alertness" refers to a specific state of active attention by high sensory awareness such as being watchful and prompt to meet danger or emergency, being quick to perceive and act.

As used herein, the term "reaction time" refers to the elapsed time between the presentation of a sensory stimulus and the subsequent behavioral response. Improved reactions times show improved (mental) processing speeds.

As used herein, the term "psychomotor control" or "psychomotor function" refers to motor action proceeding from a mental activity, also defined as movement or muscular activity associated with one or more mental processes.

In a preferred embodiment, the *Aronia* berry extract comprises more than 10% anthocyanins, even more particular comprising more than 10% anthocyanins and/or more than 30% total polyphenols and/or more than 5% cyanidin-3-glucoside. In a further embodiment, the extract of the invention comprises:

at least 10% anthocyanins;
at least 30% total polyphenols; and
at least 5% cyanidin-3-glucoside.

As disclosed before, the present invention also provides a composition comprising between 50 and 1200 mg *Aronia* berry extract, more in particular between 50 and 200 mg, even more in particular between 70 and 175 mg, even more in particular between 90 and 150 mg.

In a particular embodiment, the composition of the invention is formulated in a daily dosage form comprising at least 3 mg of anthocyanins extracted from *Aronia* berries. In particular between 5 and 40 mg anthocyanins extracted from *Aronia* berries, more in particular between 10 and 30 mg of anthocyanins, even more in particular between 12 and 20 mg of anthocyanins. In another particular embodiment, the extracts of the invention are formulated in a daily dosage form comprising at least 15 mg of anthocyanins extracted from *Aronia* berries for long term effects. The extracts of the invention are formulated in a daily dosage form comprising at least 500 mg of anthocyanins extracted from *Aronia* berries for acute effects.

In a certain embodiment, the composition comprising the *Aronia* berry extract further comprises one or more additional ingredients selected from the group consisting of: caffeine, taurine, theanine, inositol, guarana, magnesium, melatonin, ribose, carnitine, co-enzym Q10, alpha-glycerophosphocholine, alpha-lipoic acid, and xylose. It has been observed that such a combination results in a further increase in attention and reaction speed.

In a specific embodiment, the composition is an oral composition, preferably in the form of a pill, powder, capsule, tablet, gel, beverage, chewing gum, chewable tablet, lozenge or troche.

In another particular embodiment, the present invention provides a method for improving or enhancing the reaction time, attention and/or psychomotor function in a subject, the method comprising administering an *Aronia* berry extract to the subject.

The invention will now be illustrated by means of the following examples, which do not limit the scope of the invention in any way.

Example 1—Long Term Effect

A randomized, parallel, double-blind, placebo-controlled study was performed to measure the effects of an *Aronia* extract. After screening and subsequent inclusion in the study, each subject being a healthy individual between 40-60 years and having a body mass index between 25 and 35 kg/m$^2$, was assigned a unique subject identifier. Subjects were randomly assigned in a double-blind parallel fashion using random and concealed block designs, to one of the following experimental conditions:

*Aronia* extract 150 mg (i.e. 150 mg of an *Aronia melanocarpa* extract containing about 20 mg of anthocyanins)
*Aronia* extract 90 mg (i.e. 90 mg of an *Aronia melanocarpa* extract containing about 12-13 mg of anthocyanins)
Placebo The *Aronia* extract was provided in capsules of 150 or 90 mg. The placebo used in this study was maltodextrin. The capsule of the placebo had a similar/identical appearance and tasted as the *Aronia* capsule. The different capsules were ingested in a similar manner, i.e. 30 minutes before breakfast with a glass of water.

All studies are performed in the morning. Tests were taken at the baseline, after 6 weeks, after 12 weeks and after 6 months of supplementation. Tests were taken in a quiet, temperature controlled room (22° C.). Subjects were instructed to refrain from eating and drinking (except for water) after 10 pm in the evening before the test day. Furthermore, subjects were not allowed to consume any alcohol containing beverages, and to abstain from physical exercise on the day prior to testing. In addition, from two days prior to the start of the first test day until the last test day, subjects were asked not to consume any foods containing berry polyphenols. Reaction time, attention and psychomotor control were measured taking into account the results of three standardized testing methods, being a Score Out test, a Stroop test and a grooved pegboard test.

The Score Out test was used to test a person's attention, alertness and reaction time. This test is an easy and quick test to measure speed and accuracy of visual attention. Persons had to strikethrough specific numbers, while others had to be underlined. This had to be done as fast and accurate as possible. The direction is from the top of the page to the bottom which is beneficial because both left-handed and right-handed participants can evenly look ahead. A Score Out test took approximately 10 minutes.

The Stroop test was used to test participant's reaction time, attention and alertness. The Stroop tests consists of 3 cards, each containing 100 stimuli that need to be read out load as quickly and accurate as possible. The first card consists of colours in the form of words (thus the words green, red, etcetera are displayed on a card). The second card shows rectangles, again in colours. The third card is expected to ask the most from the attention and reaction time of the participants since this card contains words of colours, but these are printed in a non-corresponding colour. The participants had to say the colour instead of the word. A Stroop test took approximately 10 minutes.

The grooved pegboard test was used to measure the reaction time as well as psychomotor function. The test is a test of finger dexterity that assesses both the psychomotor speed, reaction time and fine motor control and is generally used to evaluate a number of health conditions in which hand and finger performance is of primary concern. The pegboard contains 25 holes with randomly positioned slots. The pegs, which have a key along one site, have to be rotated to match the hole before they can be inserted. This has to be done for all the slots, once with each hand. The procedure measures the performance speed in fine motor task by examining both sides of the body. A grooved pegboard test took approximately 10 minutes.

Linear mixed model analysis was used to determine the effects on this objective with fixed factors including intervention group (*Aronia* vs. placebo), time (baseline vs. 1 day, baseline vs. 6 weeks, baseline vs. 12 weeks, and baseline vs. 6 months of intervention) and intervention*time. For the variables measured at baseline, after 1 day, 6 weeks, 12 weeks, and after 6 months of intervention, an unstructured covariance structure for the repeated measures was used. Since linear mixed model analysis was used, data of dropouts were included in the statistical analysis. Missing data were not imputed. An intention-to-treat analysis (ITT) was conducted as well. The tests showed improved reaction time and attention in persons that were administered the extract of the invention compared to placebo.

Example 2—Acute/Short-Term Effect

A randomized, double-blind, placebo-controlled, crossover study was performed to measure the acute effects of the extracts of the invention. Each subject, being a healthy individual with an age between 20-65 years, was assigned a unique subject identifier. Subjects were randomly assigned in a double-blind cross-over to one of the following experimental conditions:

First intervention *Aronia* extract 500 mg (i.e. 500 mg of an *Aronia melanocarpa* extract containing ca 200 mg polyphenols); second intervention placebo 500 mg
First intervention placebo 500 mg; second intervention 500 mg *Aronia* extract.

*Aronia* extract was provided in capsules of 250 mg. The placebo used in this study was maltodextrin. The capsule of the placebo had a similar/identical appearance and tasted as the *Aronia* extract capsule. The different capsules were ingested in a similar manner, i.e. immediately after baseline measurements with a glass of water.

All studies are performed in the morning. Tests were taken at baseline and 65 min post-ingestion of the study product. Tests were taken in a quiet, temperature controlled room (22° C.). Subjects were instructed to refrain from eating and drinking (except for water) after 10 pm in the evening before the test day. In addition, from two days prior to a test day, subjects were asked not to consume any foods containing berry polyphenols. Reaction time, attention and psychomotor control were measured taking into account the results of three standardized testing methods, being a Score Out test, a Stroop test and a grooved pegboard test as indicated and explained in example 1.

Linear mixed model analysis was used to determine the effects on this objective with fixed factors including intervention group (*Aronia* vs. placebo), time (baseline vs. 70 min post-ingestion) and intervention*time. The tests showed an acutely improved reaction time and attention in persons that were administered the *aronia* extract only once, compared to placebo.

Example 3—Effect on Sports Exercise

A randomized, double-blind, placebo-controlled, crossover study was performed to measure the effects of the *aronia* extract on sports exercise related parameters. 15 healthy subjects ingested a single dose of 400 mg of *Aronia* extract, a single dose of 200 mg *Aronia* extract or Placebo. Anchored VAS questionnaires were used to detect subjective changes in various aspects of physical and mental energy along with changes in heart rate, resting energy response (REE-response) and hemodynamic parameters before, and 1, 2, and 3 hours after acute ingestion. Energy, focus, and concentration increased from baseline values in both doses with no clear dose-response effect. VAS responses in both the 200 mg and 400 mg dose increased for willingness to exercise, anxiety, motivation to train and libido increased across the measurement period. There was evidence that 200 mg and 400 mg ingestion of the *aronia* extract promoted greater changes in REE responses. Participants reported higher perception of optimism about performance and vigor and energy. After consuming a single 400 mg dose, significant group×time interaction effects were seen for energy, fatigue, and concentration. No changes in resting heart rate, systemic hemodynamics or side effect profiles were noted.

Example 4—Acute Effect

An open label short-term study was performed to measure the acute effects of the *Aronia* extract of the invention. In this study, 20 subjects were included, all experiments were performed in the morning. Tests were taken at baseline and 75 min post-ingestion of the study product. The *Aronia* extract was provided in 3 capsules containing a combined total of 1.2 g. This dose contained 575 mg total polyphenols of which 215 mg were anthocyanins. The placebo used in this study was maltodextrin. The capsule of the placebo had a similar/identical appearance and tasted as the *Aronia* capsule.

Tests were taken in a quiet, temperature controlled room (22° C.). Subjects were instructed to refrain from eating and drinking (except for water) after 10 pm in the evening before the test day. In addition, from two days prior to a test day, subjects were asked not to consume any foods containing berry polyphenols. Reaction time, attention and psychomotor control were measured taking into account the results of three standardized testing methods, being a Score Out test, a Stroop test and a Grooved pegboard test as indicated and explained in example 1.

All data were tested for normality using skewness and kurtosis. If the data were normally distributed, paired t-tests were used to analyze the differences between baseline and follow-up measurements. If the data were not normally distributed, a Wilcoxon signed rank test was used. For all tests a level of $p<0.05$ was considered to be statistically significant.

After administration of the three capsules of *Aronia* extract, the Score Out test showed a significant improvement on the four scores, Total amount correct answers (Tg), Total amount answers correct minus total mistakes (Tg-Tf), Total amount finished (Tb), and Total amount finished minus total mistakes minus total missed numbers (Tb-FoMi), that represent attention/concentration best (FIG. 1).

Figure 2:
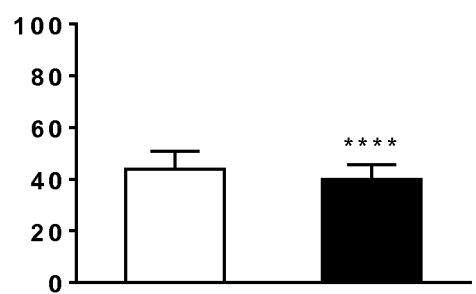
FIG. 2. Short-term effect of oral *Aronia* administration on the time needed for the Stroop test with (A) words, (B) colours and (C) words+colours. Data are expressed as mean±SD (n=19), * $P<0.001$, ** $P<0,0001$. Empty bars: baseline, black bars: treatment.
Figure 2:
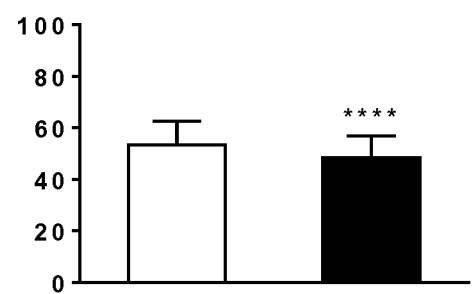
Figure 2:
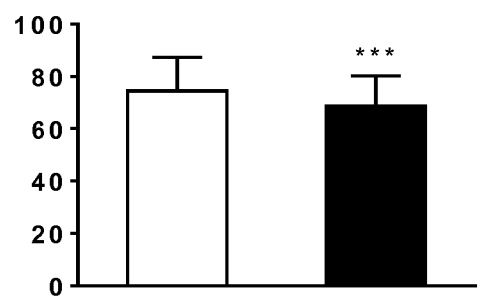

The Stroop test showed a significant decrease in the time needed to complete the tasks, indicating an improvement in overall concentration and attention (FIG. 2).

Figure 3:
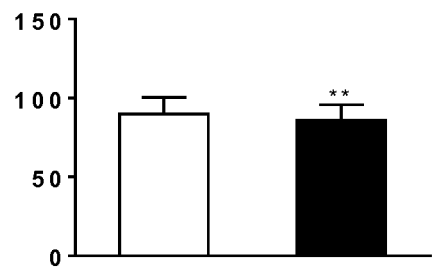
FIG. 3. Short-term effect of oral *Aronia* administration on reaction time based on the grooved pegboard test with (A) score of dominant hand and (B) score of non-dominant hand. The raw-scores have been transformed into norm-scores. Data are expressed as mean±SD (n=20),  $P<0.01$, * $P<0.001$. Empty bars: baseline, black bars: treatment.
Figure 3:
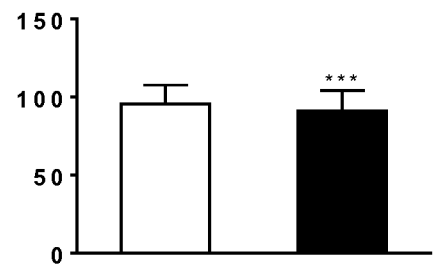

The grooved pegboard showed a significant improvement in reaction time, and hence improvement of psychomotor control, for the dominant hand as well as the non-dominant hand (FIG. 3).

Taken all together, acute effects of oral administration of the *Ariona* extract resulted in significant beneficial effects on cognitive performance. The results indicate an improvement in attention, concentration, reaction time and psychomotor control.

The invention claimed is:

1. A method for enhancing reaction time, alertness, psychomotor speed, fine motor control, and/or attention of a mammal in need thereof, the method comprising administering an *Aronia* berry extract to the mammal.

2. The method according to claim 1, wherein the *Aronia* berry extract comprises more than 10% anthocyanins.

3. The method according to claim 1, wherein the *Aronia* berry extract comprises more than 10% anthocyanins, more than 30% total polyphenols, and/or 5% cyanidin-3-glucoside.

4. The method according to claim 1, wherein the mammal is a human.

5. The method according to claim 1, wherein the mammal is a healthy human.

6. The method according to claim 1, wherein the mammal is a human, and wherein the human has an age of less than 60 years.

7. The method according to claim 1, wherein the *Aronia* berry extract is administered to enhance the reaction time of a human.

8. The method according to claim 1, wherein the *Aronia* berry extract is administered to enhance the psychomotor speed of a human.

9. The method according to claim 1, wherein the *Aronia* berry extract is administered to enhance the alertness of a human.

10. A method for enhancing reaction time, alertness, psychomotor speed, fine motor control, and/or attention of a mammal in need thereof, the method comprising administering a composition comprising an *Aronia* berry extract to the mammal.

11. The method according to claim 10, wherein the composition comprises between 50-1200 mg of the *Aronia* berry extract.

12. The method according to claim 10, wherein the composition comprises the *Aronia* berry extract in combination with one or more additional ingredients selected from the group consisting of: caffeine, taurine, theanine, inositol, guarana, magnesium, melatonin, ribose, carnitine, co-enzyme Q10, alpha-glycerophosphocholine, alpha-lipoic acid, and xylose.

13. The method according to claim 10, wherein the composition is formulated in a daily dosage form comprising 5 to 500 mg of anthocyanins extracted from *Aronia* berries.

14. The method according to claim 10, wherein the composition is an oral composition.

15. The method according to claim 10, wherein the composition is in the form of a pill, powder, capsule, tablet, gel, beverage, chewing gum, chewable tablet, lozenge, or troche.

16. The method according to claim 10, wherein the *Aronia* berry is an *Aronia melanocarpa* berry.

* * * * *